US008685081B2

(12) United States Patent
Yamagata

(10) Patent No.: US 8,685,081 B2
(45) Date of Patent: Apr. 1, 2014

(54) MEDICAL STENT OF RESIN MATERIAL

(75) Inventor: Toshihiro Yamagata, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/483,564

(22) Filed: May 30, 2012

(65) Prior Publication Data
US 2012/0330433 A1 Dec. 27, 2012

Related U.S. Application Data

(63) Continuation of application No. PCT/JP2011/074931, filed on Oct. 28, 2011.

(30) Foreign Application Priority Data

Oct. 29, 2010 (JP) ................................ P2010-244230

(51) Int. Cl.
A61F 2/04 (2013.01)
(52) U.S. Cl.
USPC ...................... 623/1.44; 623/23.64; 623/23.71
(58) Field of Classification Search
USPC ........................ 623/1.14, 1.44, 23.64–23.66, 623/23.69–23.71; 604/8
See application file for complete search history.

(56) References Cited

U.S. PATENT DOCUMENTS

| 5,282,860 | A | 2/1994 | Matsuno et al. | |
| 5,514,176 | A | 5/1996 | Bosley | |
| 6,383,214 | B1* | 5/2002 | Banas et al. | 623/1.14 |
| 2002/0038142 | A1 | 3/2002 | Khosravi et al. | |
| 2002/0143384 | A1 | 10/2002 | Ozasa | |
| 2004/0210300 | A1 | 10/2004 | Aboul-Hosn | |
| 2008/0051911 | A1* | 2/2008 | Rucker | 623/23.7 |
| 2008/0086214 | A1* | 4/2008 | Hardin et al. | 623/23.7 |
| 2009/0148591 | A1* | 6/2009 | Wang et al. | 427/2.25 |

FOREIGN PATENT DOCUMENTS

| EP | 0 716 834 A1 | 6/1996 |
| JP | 10-305050 A | 11/1998 |
| JP | 11-276599 A | 10/1999 |
| JP | 2001-187149 A | 7/2001 |

(Continued)

OTHER PUBLICATIONS

Japanese Office Action dated Oct. 2, 2012 from corresponding Japanese Patent Application No. JP 2012-525551, together with an English language translation.

(Continued)

Primary Examiner — David Isabella
Assistant Examiner — Dinah Baria
(74) Attorney, Agent, or Firm — Scully, Scott, Murphy & Presser, P.C.

(57) ABSTRACT

The medical stent includes: a main body formed into an approximately tubular shape along a longitudinal axis with a first resin material; an elastic member formed of a second resin material which is larger in flexural modulus than the first resin material, and configured to have one end portion connected to an end portion of the main body and the other end portion formed to extend to the central portion side of the main body along the longitudinal axis and also to direct to the radial direction of the main body; and a treated layer formed between the end portion of the main body and the one end portion of the elastic member and configured to have a functional group for joining the end portion of the main body and the one end portion of the elastic member to each other.

5 Claims, 5 Drawing Sheets

(56) References Cited

FOREIGN PATENT DOCUMENTS

| | | |
|---|---|---|
| JP | 2002-355316 A | 12/2002 |
| JP | 2004-531289 A | 10/2004 |
| JP | 2005-278993 A | 10/2005 |
| JP | 2006-87712 A | 4/2006 |
| JP | 2007-20635 A | 2/2007 |
| JP | 2007-515249 A | 6/2007 |
| JP | 2010-537743 A | 12/2010 |
| WO | WO 02/38084 A2 | 5/2002 |
| WO | WO 2005/065581 A1 | 7/2005 |
| WO | WO 2009/029744 A1 | 3/2009 |
| WO | WO 2009/145901 A1 | 12/2009 |

OTHER PUBLICATIONS

European Search Report dated Jan. 22, 2013 from corresponding European Patent Application No. EP 11 83 6446.2.

International Search Report PCT/JP2011/074931 dated Jan. 31, 2012 together with an English language translation.

* cited by examiner

MEDICAL STENT OF RESIN MATERIAL

BACKGROUND OF THE INVENTION

1. Field of the Invention

The present invention relates to a medical stent and a production method of a medical stent. This application is a continuation application based on PCT Patent Application No. PCT/JP2011/074931, filed on Oct. 28, 2011, claiming priority based on Japanese Patent Application No. 2010-244230, filed on Oct. 29, 2010, the contents of both the Japanese Patent Application and the PCT Application are incorporated herein by reference.

2. Background Art

Conventionally, in order to dilate a narrowed area formed at a lumen in living body, such as a blood vessel, a digestive tract, or a bile duct and maintain the opened state, a medical stent (hereinafter also referred to as a "stent") has been indwelled at the narrowed area.

Among them, for example, a stent which is used for a bile duct, as shown in Japanese Unexamined Patent Application Publication No. 2006-87712, is formed in an approximately tubular shape. Flaps (elastic members) which are opened in a natural state and deformed so as to be closed by a given external force are respectively provided at the distal end side and the proximal end side of the stent. The flaps are formed by cutting and raising a member made of resin, which is used in the outer circumferential surface of a main body of the stent.

These flaps are locked to an inlet port of a duodenal papilla and an outlet port of a narrowed area of a bile duct, thereby fixing the stent to the narrowed area. Subsequently, the stent is collected with use of a portion locked to the inlet port of the duodenal papilla in the stent.

A stent having another configuration shown in Japanese Unexamined Patent Application Publication No. 2005-278993 is not provided with a flap and is constituted by connecting a plurality of materials to each other. This stent is provided with a stent main body formed in an approximately cylindrical shape and having a plurality of openings formed therein, a coating resin layer disposed in an inner cavity of the stent main body and formed of a porous resin film, and a tubular cover which connects the stent main body and the coating resin layer to each other.

The tubular cover is formed of thermosetting resin or the like having no adhesiveness with porous resin. The stent main body is subjected to primer treatment in order to enhance adhesiveness with the thermosetting resin. The tubular cover is connected to the coating resin layer by flowing a solution of thermosetting resin dissolved in an organic solvent into pores formed in the porous resin film and then solidifying it.

Further, a stent transplantation piece described in Japanese Unexamined Patent Application Publication No. H10-305050 is also not provided with a flap, and a lattice member formed in a tubular shape and a sleeve disposed so as to cover the outer circumferential surface of the lattice member are connected to each other by a silicone adhesive.

SUMMARY OF THE INVENTION

According to a first aspect of the invention, a medical stent including: a main body configured to have a longitudinal axis and formed into an approximately tubular shape along the longitudinal axis with a first resin material; an elastic member formed of a second resin material which is larger in flexural modulus than the first resin material in order to be locked to an inner wall of a lumen in living body and configured to have one end portion connected to an end portion of the main body and the other end portion formed to extend to the central portion side of the main body along the longitudinal axis and also to direct to outside in the radial direction of the main body. And a treated layer formed between the end portion of the main body and the one end portion of the elastic member and configured to have a functional group for joining the end portion of the main body and the one end portion of the elastic member to each other.

According to a second aspect of the invention, in the medical stent related to the first aspect, the melting temperature of the second resin material is higher than the melting temperature of the first resin material and the end portion of the main body and the one end portion of the elastic member are connected to each other at a temperature equal to or higher than the melting temperature of the first resin material and lower than the melting temperature of the second resin material.

In addition, the melting temperature as referred to herein means a temperature when a load is set to be 2.16 kg, the amount of resin flowing out from a pore in 10 minutes becomes 0.2 g in which Japanese Standards Association defines as JIS K7210: a melt mass flow rate (MFR) test method of thermoplastics.

According to a third aspect of the invention, in the medical stent related to the second aspect, the second resin material is fluororesin and the treated layer is formed by chemically treating and reforming the outer circumferential surface of the one end portion of the elastic member.

According to a fourth aspect of the invention, in the medical stent related to the third aspect, the first resin material is polyurethane resin and a hydroxy group or a carbonyl group formed in the treated layer is bonded to a functional group of the polyurethane resin.

According to a fifth aspect of the invention, the medical stent related to the third aspect further includes: a coil formed by winding a wire around a predetermined given axis and also provided on the inner circumference side of the main body coaxially with the main body; and an inner layer formed in an approximately tubular shape and provided on the inner circumference side of the coil coaxially with the main body.

According to a sixth aspect of the invention, in the medical stent related to the third aspect, an odd number of the elastic members are provided with equal angles therebetween around the longitudinal axis and one of the elastic members is disposed to avoid the opposing positions of the other elastic members.

According to a seventh aspect of the invention, the medical stent related to the third aspect further includes: a fixing member mounted on the outer circumferential surface of the one end portion of the elastic member and the outer circumferential surface of the main body and formed into a tubular shape with the first resin material, wherein the outer circumferential surface of the main body and the inner circumferential surface of the fixing member are welded to each other, the treated layer is formed at the one end portion of the elastic member, and the treated layer of the elastic member and the inner circumferential surface of the fixing member are connected to each other at a temperature equal to or higher than the melting temperature of the first resin material and lower than the melting temperature of the second resin material.

According to an eighth aspect of the invention, a production method of a medical stent including: a first step of forming a main body with a first resin material into an approximately tubular shape along a longitudinal axis; a second step of forming a treated layer configured to have a functional group, at one end portion of an elastic member formed of a second resin material which is larger in flexural modulus than the first resin material, by carrying out surface treatment for joining one end portion of the elastic member to an end portion of the main body; and a third step of joining the end portion of the main body and the one end portion of the elastic member to each other by pressing the one end portion of the elastic member configured to have a functional group and subjected to the surface treatment and the end portion of the main body against each other while applying heat.

PREFERRED EMBODIMENTS

Hereinafter, a stent according to an embodiment of the invention will be described with reference to FIGS. 1 to 9.

A stent is indwelled in the bile duct of a living body by a stent delivery catheter or the like which is used endoscopically. In all of the following drawings, in order to make it easy to see the drawings, the thicknesses or the ratios of the dimensions of the respective constituent elements are varied appropriately.

Figure 1:
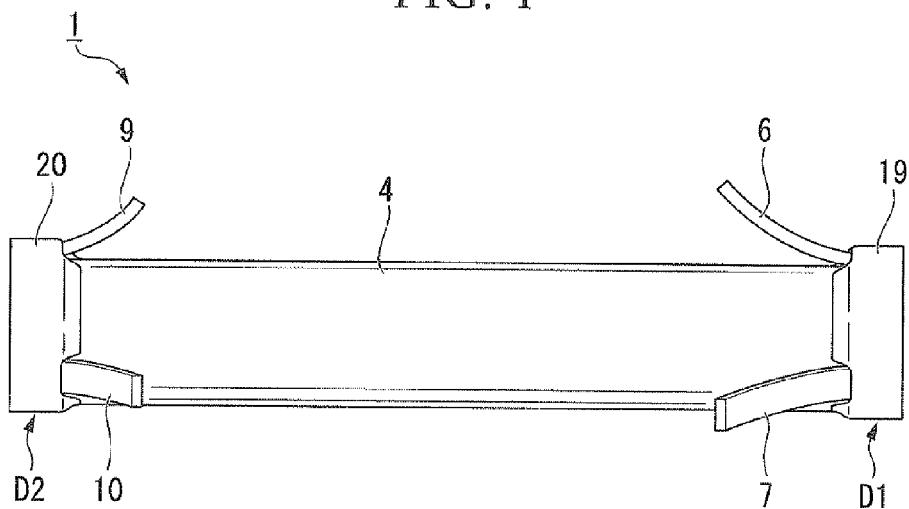
FIG. 1 is a side view of a medical stent according to an embodiment of the invention.
Figure 2:
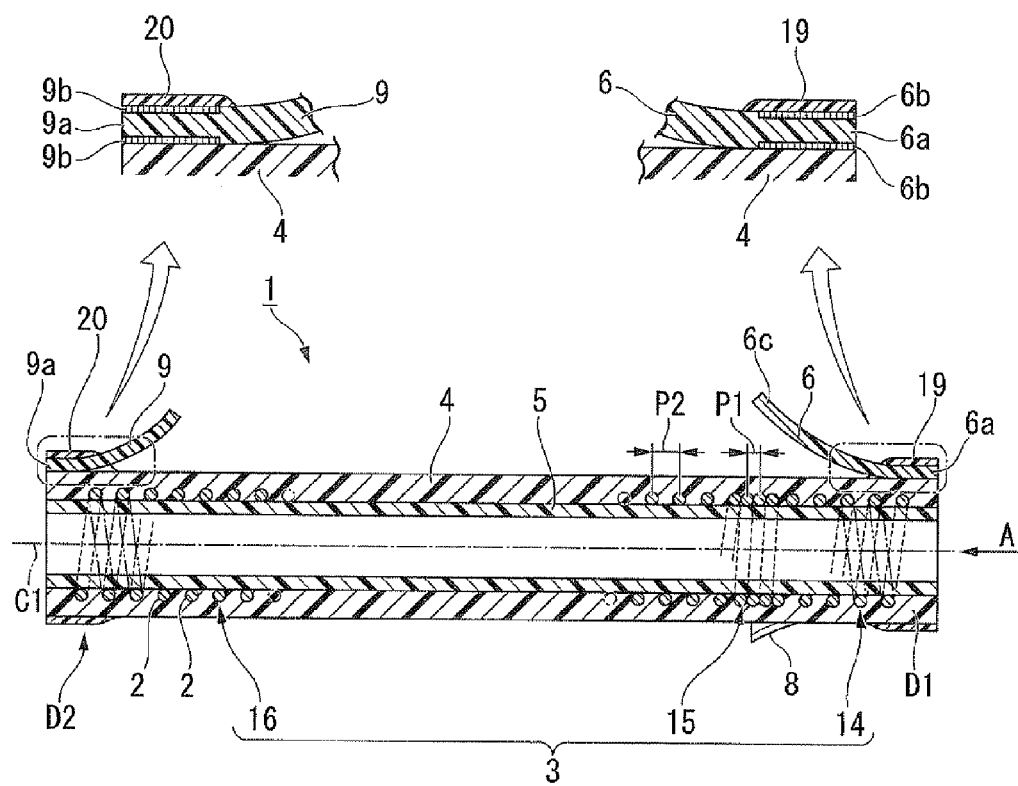
FIG. 2 is a vertical cross-sectional view and partially enlarged views of the medical stent according to the embodiment of the invention.

As shown in FIGS. 1 and 2, a stent 1 of the embodiment includes a coil 3 formed by winding a wire 2 around an axis (a longitudinal axis) C1, an outer layer (a main body) 4 formed in an approximately tubular shape and provided on the outer circumference side of the coil 3 coaxially with the coil 3, an inner layer 5 formed in an approximately tubular shape and provided on the inner circumference side of the coil 3 coaxially with the coil 3, and flaps (elastic members) 6 to 11 (the flap 11 is not shown in the drawings) each formed in the form of a plate and fixed to the outer circumferential surface of the outer layer 4.

The stent 1 is inserted into the bile duct from a distal end side D1 where the three flaps 6 to 8 are provided.

The wire 2 is formed of metal such as tungsten steel or stainless steel, which is a radiopaque material. The cross-section of the wire 2 is formed in a circular shape. In the present embodiment, the wire 2 configured to have an outer diameter of, for example, 0.11 mm is used. The coil 3 is constituted by connecting a normally wound coil 14, a marker coil 15, and a normally wound coil 16, in which the winding pitches of the wire 2 are changed, to each other side by side in this order in a direction of the axis C1 from the distal end side D1 to a proximal end side D2.

The marker coil 15 is formed by winding the wire 2 around the axis C1 in approximately close coiling. In addition, the term "approximately close coiling" as referred to herein means that the wire 2 is wound at a pitch of a constant value greater than or equal to one times the outer diameter of the wire 2 and less than or equal to seven times the outer diameter of the wire 2. In this embodiment in which the wire 2 having an outer diameter of for example, 0.11 mm is used, a clearance greater than or equal to 0.01 mm and less than or equal to 0.08 mm is provided between adjacent wires 2 in the marker coil 15, so that a pitch P1 of the wire 2 becomes greater than or equal to 0.12 mm and less than or equal to 0.19 mm. At this time, the pitch P1 of the wire 2 becomes greater than or equal to about 1.1 times the outer diameter of the wire 2 and less than or equal to 1.7 times the outer diameter of the wire 2. In addition, for convenience of explanation, this clearance is not shown in the drawings.

By providing the clearance in this manner, at a portion in which the marker coil 15 is formed, the outer layer 4 and the inner layer 5 are connected to each other in a clearance portion between adjacent wires 2, so that the outer layer 4 and the inner layer 5 are not easily separated from each other.

Then, the central portion of the marker coil 15 in the direction of the axis C1 is disposed so as to conform to end portions (free ends which will be described later) on the proximal end side D2 of the flaps 6 to 8.

It is preferable that a pitch P2 of the wire 2 in the normally wound coils 14 and 16 is a pitch greater than or equal to two times and less than or equal to twenty times the pitch P1 of the wire 2 in the marker coil 15.

If a difference between the pitches of the wire 2 is less than two times, it becomes difficult to distinguish between the marker coil 15 and the normally wound coils 14 and 16 under fluoroscopic control of X-ray. Further, if the difference between the pitches exceeds twenty times, it becomes not possible to retain the size of an inner cavity of the inner layer 5 when the stent 1 is bent.

The outer layer 4 is formed of polyurethane resin (a first resin material) having a Shore hardness of 70 D or less. The outer layer 4 is provided not only on the outer circumferential surface of the coil 3, but also in the clearances between the wires 2. The polyurethane resin has non-crystallinity and the melting temperature of the polyurethane resin having the Shore hardness of 70 D or less is in a range of 100° C. to 250° C.

The inner layer 5 is formed of PFA (perfluoroalkoxylalkane), FEP, PTFE (polytetrafluoroethylene), or the like, which are fluororesin and have elasticity.

It is preferable that the coil 3, the outer layer 4, and the inner layer 5 which are formed integrally have biocompatibility and be also constituted to be soft (to have small resiliency) compared to the flaps 6 to 11.

The flaps 6 to 11 are formed of fluororesin (a second resin material), which is a material different from polyurethane resin. In the fluororesin, PTFE, PFA, PVDF, or the like is included. The melting temperature of PFA is about 380° C.

As shown in the partially enlarged view in FIG. 2, on the outer circumferential surface on a fixed end (one end) 6a side of the flap 6, which is fixed to the outer layer 4, a known chemical treatment using a metal sodium solution is carried out, so that a surface reforming is performed. On the outer circumferential surface on the fixed end 6a side, a surface-treated section (a treated layer) 6b configured to have a functional group effective for adhesion (connection) is formed, and also surface roughness (arithmetic mean roughness: Ra) is made large.

The chemical treatment is a treatment of making some of the fluorine molecules break away from the carbon skeleton of the fluororesin by chemical reaction and forming a hydroxy group (a hydroxyl group), a carbonyl group, or the like effective for adhesion at a breakaway portion. In the chemical treatment, for example, Tetra Etch (a registered trademark, manufactured by Junkosha, Inc.) or the like is suitably used.

Similarly, surface-treated sections are also formed on the outer circumferential surfaces on the fixed end sides of the flaps 7 to 11. In the partially enlarged view in FIG. 2, only a surface-treated section 9b on a fixed end 9a side of the flap 9 is shown.

The flap 6 is fixed with the surface-treated section 6b brought into contact with the outer circumferential surface of an end portion on the distal end side D1 in the outer layer 4. In addition, on the flap 6, a treatment such as imposing a shape in advance is carried out. Further, the flap 6 is formed such that a free end (the other end) 6c is opened to the radial outside of the outer layer 4 while extending to the central portion side of the outer layer 4 along the axis C1.

The surface-treated section 6b and the outer circumferential surface of the outer layer 4 are pressed against each other at a temperature equal to or higher than the melting temperature of the polyurethane resin and lower than the melting temperature of the fluororesin. Then, the surface-treated section 6b and the outer circumferential surface of the outer layer 4 are connected to each other by an anchor effect in which a portion of the melted outer layer 4 penetrates into the rough surface of the surface-treated section 6b, and by hydrogen bonds or chemical reaction (chemical bonds) between a hydroxy group or a carbonyl group of the surface-treated section 6b and a high affinity functional group of the outer layer 4.

By pressing the surface-treated section 6b and the outer layer 4 against each other at a temperature equal to or higher than the melting temperature of the polyurethane resin and lower than the melting temperature of the fluororesin, the flap 6 is prevented from being deformed or melted and the outer layer 4 is deformed, so that the surface-treated section 6b and the outer layer 4 are connected to each other.

The three flaps 6 to 8 are disposed with equal angles therebetween, that is, every 120° around the axis C1.

The flaps 7 and 8 are formed such that surface-treated sections (not shown) are fixed to the end portion on the distal end side D1 in the outer layer 4 and also free ends are opened to the radial outside of the outer layer 4 while extending to the central portion side of the outer layer 4 along the axis C1, similarly to the flap 6.

Figure 3:
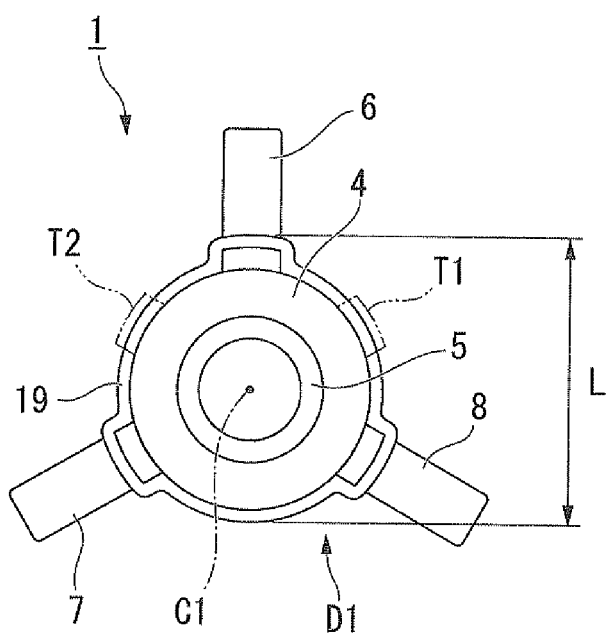
FIG. 3 is a view as seen in a direction of arrow A in FIG. 2.

Then, each of the flaps 6 to 8 is disposed to avoid the opposing positions sandwich the axis C1 of the others of the flaps 6 to 8. For example, as shown in FIG. 3, the flap 6 is disposed to avoid opposing positions T1 and T2 sandwich the axis C1 of the flaps 7 and 8.

As shown in FIGS. 1 and 2, the three flaps 9 to 11 are fixed with the surface-treated sections being brought into contact with the outer circumferential surface of an end portion on the proximal end side D2 in the outer layer 4, similarly to the flaps 6 to 8. The three flaps 9 to 11 are formed such that free ends which become end portions on the opposite side to the fixed end 9a are opened to the radial outside of the outer layer 4 while being extended.

The flaps 9 to 11 are set such that length in a longitudinal direction are shorter than length in a longitudinal direction of the flaps 6 to 8.

The flaps 9 to 11 are disposed with equal angles therebetween around the axis C1. The flaps 9 to 11 are disposed such that the flap 9 and the flap 6, the flap 10 and the flap 7, and the flap 11 and the flap 8 respectively overlap each other when viewed parallel to the axis C1.

As shown in FIGS. 2 and 3, in the present embodiment, a fixing member 19 formed in a tubular shape is mounted so as to cover the outer circumferential surfaces on the fixed end sides of the flaps 6 to 8 and the outer circumferential surface on the distal end side D1 of the outer layer 4. The fixing member 19 is formed of the same resin material as that of the outer layer 4.

The outer circumferential surface of the outer layer 4 and the inner circumferential surface of the fixing member 19 are welded to each other at a temperature equal to or higher than the melting temperature of the polyurethane resin.

The surface-treated section 6b of the flaps 6 to 8 and the inner circumferential surface of the fixing member 19 are pressed against each other at a temperature equal to or higher than the melting temperature of the polyurethane resin and lower than the melting temperature of the fluororesin, thereby being connected to each other by an anchor effect, chemical bonds, and the like.

Similarly to the fixing member 19, a fixing member 20 formed in a tubular shape is mounted so as to cover the outer circumferential surfaces on the fixed end sides of the flaps 9 to 11 and the outer circumferential surface on the proximal end side D2 of the outer layer 4.

The fixing member 20 is connected to the outer circumferential surfaces on the fixed end sides of the flaps 9 to 11 and also welded to the outer circumferential surface on the proximal end side D2 of the outer layer 4, similarly to the fixing member 19. Since the fixing member 20 has the same configuration as that of the fixing member 19, a detailed description is omitted.

Next, an motion of the stent 1 configured as described above will be described below with the procedure of placing the stent 1 in the bile duct taken as an example.

Figure 4:
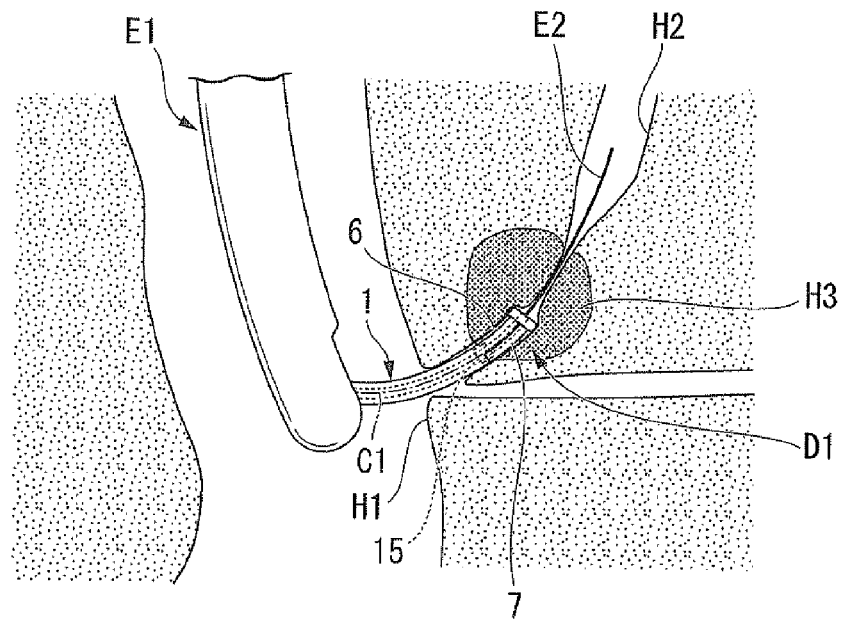
FIG. 4 is a diagram showing an operation during use of the medical stent according to the embodiment of the invention.

First, a user inserts a side-viewing type endoscope through a natural opening such as mouth or the like into the body cavity of a patient and advances a distal end of an endoscope E1 up to the vicinity of a duodenal papilla H1, as shown in FIG. 4.

Next, the user inserts a guide wire E2 through a forceps opening (not shown) of the endoscope E1 and makes a distal end of the guide wire E2 protrude toward the duodenal papilla H1 while appropriately manipulating a raising stand (not shown).

Then, the user inserts the distal end of the guide wire E2 through the duodenal papilla H1 into a bile duct H2.

Figure 5:
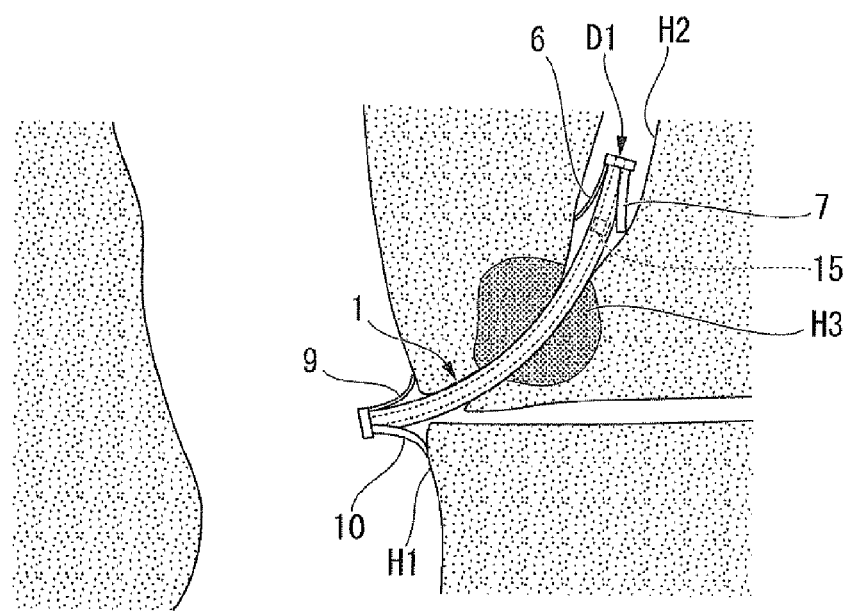
FIG. 5 is a diagram showing an motion during use of the medical stent according to the embodiment of the invention.

Further, the user confirms the duodenal papilla H1 and the shape of a narrowed area H3 of the bile duct H2 under fluoroscopic control of X-ray. In addition, in the present embodiment, as shown in FIG. 5, the stent 1 is used in which in a state where the respective flaps 6 to 11 are opened, the length in the direction of the axis C1 from the free end of each of the flaps 6 to 8 to the free end of each of the flaps 9 to 11 is approximately equal to the length from the duodenal papilla H1 to a site going beyond the narrowed area H3 of the bile duct H2.

Next, the user inserts the stent 1 into the bile duct H2 from the distal end side D1 along the guide wire E2 by using a stent delivery catheter (not shown) inserted through the forceps opening, while confirming the marker coil 15 of the stent 1 and the position and the shape of the bile duct H2 under fluoroscopic control of X-ray.

When the distal end side D1 of the stent 1 reaches the narrowed area H3 of the bile duct H2, the flaps 6 to 8 are pressed toward the axis C1 by the narrowed area H3. When the stent 1 is further inserted into the bile duct H2, so that the flaps 6 to 8 cross over the narrowed area H3, as shown in FIG. 5, the free end sides of the flaps 6 to 8 are opened, so that the flaps 6 to 8 are locked to the narrowed area H3.

At this time, since the stent 1 in which the length in the direction of the axis C1 from the free end of each of the flaps 6 to 8 to the free end of each of the flaps 9 to 11 is set as described above is used, the flaps 9 to 11 are also locked to the duodenal papilla H1.

Next, the user extracts the endoscope E1 and the guide wire E2 from the body cavity of the patient, thereby finishing a series of procedures.

For the main body 4 such as the outer layer in the stent, ease of bending is required in order to follow the shape of a lumen of a living body or the motion of the living body. On the other hand, for the flap, a certain hardness is required in order to make the flap be reliably locked to the living body. For this reason, in the case of welding the flap to the main body, members which are relatively large in hardness difference are welded to each other.

When welding two members to each other, it is preferable to weld the members to each other in a state where both the members are melted to some extent. In general, since the higher the hardness of a material, the higher the melting temperature of the material becomes, a difference in melting temperature between members which are large in hardness difference becomes large. Since the temperature when welding members which have a large hardness difference with respect to each other is set to be equal to or higher than the melting temperature of the member having higher melting temperature, the member having lower melting temperature is heated up to a temperature significantly higher than its own melting temperature, thereby being strongly affected by heat.

Further, in a case where a part of the flaps have been thermally welded to the main body, the vicinity of a welded portion is partially crystallized, thereby becoming hard.

In the stent 1 of the present embodiment, a portion of the melted outer layer 4 is connected to the surface-treated section 6*b* by pressing the surface-treated section 6*b* of the flap 6 and the outer circumferential surface of the outer layer 4 against each other at a temperature equal to or higher than the melting temperature of the polyurethane resin and lower than the melting temperature of the fluororesin.

For this reason, when mounting the flap 6 on the outer layer 4, deformation or melting of the flap 6 is prevented. Even in a case where the outer layer 4 and the flap 6 formed of different materials are connected to each other, crystallization and hardening of the surface-treated section 6*b* of the flap 6 is prevented. Conventionally, in a case where a flap has been crystallized and hardened, there has been a possibility that fracture may occur from the interface of a crystallized portion when the flap is deformed repeatedly.

Therefore, it is possible to reliably connect the surface-treated section 6*b* of the flap 6 to the outer circumferential surface of the outer layer 4, thereby making the stent 1 be locked to the narrowed area H3 of the bile duct H2 over a longer period of time. That is, it is possible to prevent the stent 1 from moving from the inside of the bile duct with the stent 1 indwelled, thereby moving to an unexpected place.

Further, since the flap 6 is a separate member from the outer layer 4, it is possible to set the hardness, the resiliency, or the like of the flap 6 and the outer layer 4 independently from each other.

Since the flap 6 is formed of fluororesin having a large flexural modulus among resin materials, it is possible to make the flap 6 be reliably locked to the narrowed area H3 of the bile duct H2. Since the surface of the fluororesin is small in frictional resistance, it is possible to improve insertability when inserting the stent 1 into a channel of an endoscope, for example.

Further, on the outer circumferential surface on the fixed end 6*a* side of the flap 6, the surface-treated section 6*b*, which is subjected to the chemical treatment using a metal sodium solution, thereby having a roughened surface, is formed. For this reason, when the surface-treated section 6*b* and the outer circumferential surface of the outer layer 4 are pressed against each other at a predetermined temperature, the melted outer layer 4 penetrates into the rough surface of the surface-treated section 6*b*, so that the surface-treated section 6*b* of the flap 6 may be more reliably connected to the outer layer 4. The chemical treatment in an embodiment of the present invention is the treatment of replacing a fluorine molecule of a carbon skeleton with a hydroxy group or the like without forming a layer so as to be newly layered on the outer circumferential surface on the fixed end 6*a* side of the flap 6. Therefore, it is possible to suppress an increase in the outer diameter of a portion where the surface-treated section 6*b* and the outer layer 4 are adhered to each other.

Since a hydroxy group or a carbonyl group formed in the surface-treated section 6*b* hydrogen-bonds to or chemically reacts with a high affinity functional group of the outer layer 4, it is possible to more reliably connect the surface-treated section 6*b* of the flap 6 to the outer layer 4.

The three flaps 6 to 8 are provided with equal angles therebetween around the axis C1 and each flap is disposed to avoid the opposing positions of the other flaps. For this reason, as shown in FIG. 3, the dimension of an outer diameter L of the stent 1 at a portion where the flaps 6 to 8 are provided is kept small, so that it is possible to improve insertability when inserting the stent 1 into a channel of a stent delivery catheter, an endoscope, or the like. Further, in a case where the outer diameter of the stent 1 is constant, it is possible to make the inner diameter of the stent 1 large.

Since the fixing member 19 is mounted on the outer circumferential surfaces on the fixed end sides of the flaps 6 to 8 and the outer circumferential surface of the outer layer 4, it is possible to more reliably fix the fixed ends of the flaps 6 to 8 to the outer circumferential surface of the outer layer 4.

Further, by disposing the flaps 6 to 8 so as to extend along the axis C1 and mounting the fixed ends to an end portion on the distal end side D1 in the outer layer 4, it is possible to harden the stent 1 at a portion with the flaps 6 to 8 mounted thereon. For this reason, it is possible to improve insertability into the narrowed area H3 of the bile duct H2 on the distal end side D1 of the stent 1. In addition, by shifting a position where the fixed ends of the flaps 6 to 8 and the outer circumferential surface of the outer layer 4 are fixed to each other, to the central portion side in the direction of the axis C1, it is possible to adjust the stiffness of the distal end side D1 of the stent 1.

In addition, the flap 6 in the present embodiment may be modified into various configurations as described below.

Figure 6:
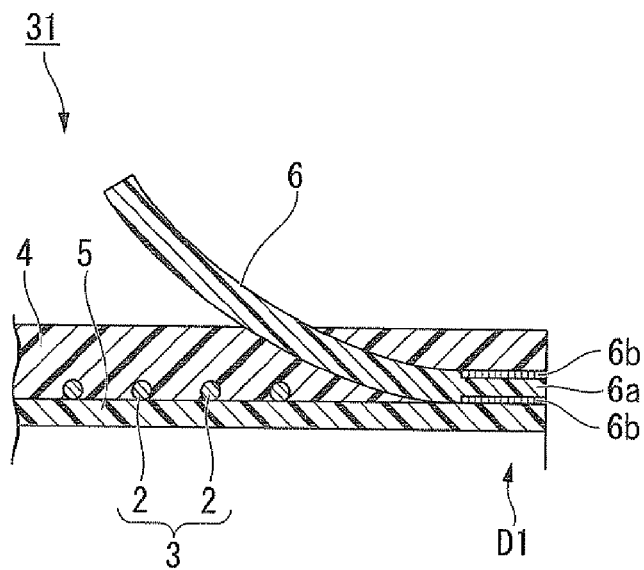
FIG. 6 is a cross-sectional view of a main section of a medical stent in a modified example of the embodiment of the invention.

For example, in the stent 1 of the present embodiment, although the fixing member 19 is provided, a configuration is also acceptable in which the fixing member 19 is not provided and the fixed end 6*a* of the flap 6 is directly connected to the outer circumferential surface of the inner layer 5, as in a stent 31 in a modified example shown in FIG. 6. According to such a configuration, it is possible to keep the dimension of the outer diameter in the distal end side D1 of the stent 31 small.

Figure 7:
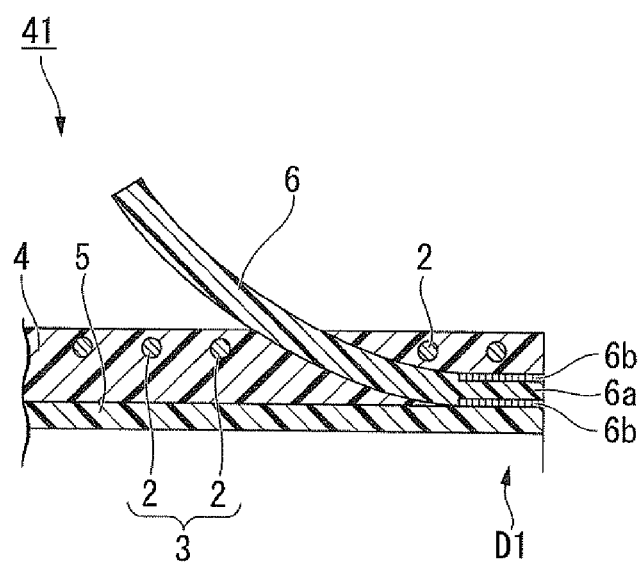
FIG. 7 is a cross-sectional view of a main section of a medical stent in a modified example of the embodiment of the invention.

As in a stent 41 shown in FIG. 7, with respect to the stent 31 in the above modified example, the flap 6 may also be disposed so as to pass between adjacent wires 2. According to such a configuration, the same effect as that of the stent 31 in the above modified example is obtained and it is also possible to dispose the wire 2 up to the distal end side D1 of the stent 41. It is possible to lengthen the length of the stent 41, which is visible under fluoroscopic control of X-ray. Further, in the stent 41 of the modified example, the fixed end 6a of the flap 6 may also be directly connected to the outer surface of the coil 3.

Figure 8:
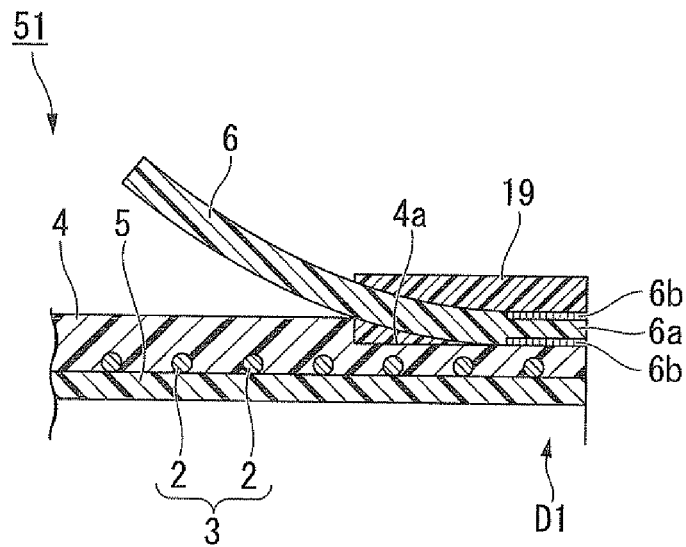
FIG. 8 is a cross-sectional view of a main section of a medical stent in a modified example of the embodiment of the invention.

Further, as in a stent 51 shown in FIG. 8, with respect to the stent 1 of the present embodiment, a concave portion 4a may also be formed in the outer circumferential surface on the distal end side D1 of the outer layer 4. The fixed end 6a of the flap 6 may be connected to the concave portion 4a and the fixed end 6a of the flap 6 may be also covered by the fixing member 19. According to such a configuration, it is possible to keep the dimension of the outer diameter in the distal end side D1 of the stent 51 small.

Figure 9:
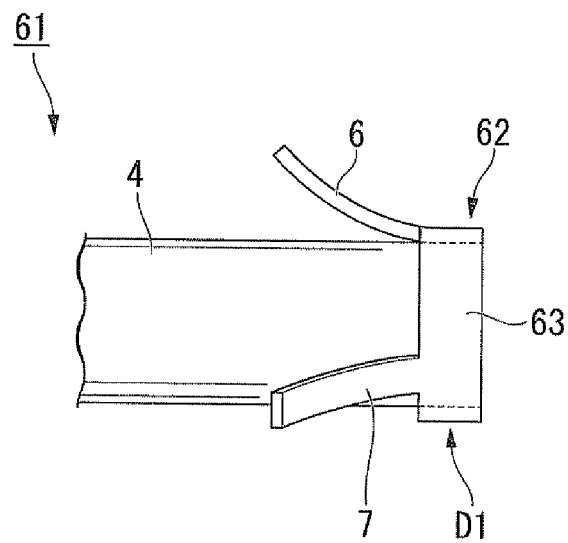
FIG. 9 is a side view of a main section of a medical stent in a modified example of the embodiment of the invention.

In the stent 1 of the present embodiment, although the fixing member 19 is provided, a configuration is also acceptable in which the fixing member 19 is not provided and a flap section 62 is formed by integrating the flaps 6 to 8, as in a stent 61 in a modified example shown in FIG. 9. The flap section 62 has the flaps 6 to 8 described above and a tubular connecting member 63 connected to the fixed ends of the flaps 6 to 8. In this modified example, the flaps 6 to 8 and the connecting member 63 are integrally formed of fluororesin or the like. A surface-treated section (not shown) is formed on the inner circumferential surface of the connecting member 63 and the surface-treated section of the flap section 62 and the outer circumferential surface of the outer layer 4 are connected to each other by chemical bonds.

According to such a configuration, even if the fixing member 19 is not provided, it is possible to reliably connect the flaps 6 to 8 to the outer circumferential surface of the outer layer 4 and suppress the dimension of the outer diameter in the distal end side D1 of the stent 61 small.

The embodiment of the invention has been described in detail above with reference to the drawings. However, a specific configuration is not limited to the embodiment and change or the like of the configuration within the scope which does not depart from the spirit of the invention is also included.

For example, in the present embodiment, the three flaps 6 to 8 are disposed with equal angles therebetween around the axis C1. However, the number of flaps which are provided on the distal end side D1 of the stent 1 is not limited as long as each flap is disposed to avoid the opposing positions sandwich the axis C1 of the other flaps. However, when the number of flaps which are provided on the distal end side D1 is an odd number, even if the flaps are provided with equal angles therebetween around the axis C1, since each flap is not disposed at the opposing positions of the other flaps, this is more preferable.

Further, with respect to the six flaps 6 to 11, it is preferable that each flap be disposed to avoid the opposing positions of the other five flaps when viewed parallel to the direction of the axis C1. By configuring the flaps 6 to 11 in this manner, it is possible to keep the dimension of the outer diameter of the stent 1 small in any radial direction over the entire length of the stent 1 when viewed parallel to the direction of the axis C1.

Further, in the above-described embodiment, in a case where the connection strength between the flaps 6 to 8 and the outer layer 4 can be secured sufficiently, the stent 1 need not be provided with the fixing member 19. According to such a configuration, it is possible to reduce the outer diameter of the stent 1 at a portion where the flaps 6 to 8 are provided.

If the flap 6 and the outer layer 4 are pressed against each other at a temperature equal to or higher than the melting temperature of the polyurethane resin and lower than the melting temperature of the fluororesin, the outer layer 4 is deformed. Therefore, a depression corresponding to the shape of the flap 6, that is, a housing portion when the flap 6 has been pressed toward the axis C1 by the above-described narrowed area H3 by pressing the flap 6 and the outer layer 4 against each other may also be formed in the outer circumferential surface of the outer layer 4.

In the above-described embodiment, the outer layer 4 is formed of polyurethane resin. However, a material for forming the outer layer 4 is not limited thereto. As the first resin material, for example, polyamide-based elastomer, polyethylene-based elastomer, soft polyethylene, polystyrene-based elastomer, polyester-based elastomer, or the like can be used appropriately.

Further, as a material (the second resin material) for forming the flaps 6 to 11, polyether ether ketone resin or the like can be appropriately used without being limited to fluororesin.

In the above-described embodiment, the coil 3 is provided with the marker coil 15 in which the wire 2 is wound in close coiling. However, this is not an essential configuration. It is acceptable if the outline of the coil 3 can be seen under fluoroscopic control of X-ray.

The preferred examples of the invention have been described above. However, the invention is not limited thereto. Addition, omission, substitution, and other changes of a configuration can be made within the scope which does not depart from the spirit of the invention. The invention is not limited by the above-mentioned description, but limited only in the scope of the appended claims.

The invention claimed is:
1. A medical stent comprising:
a main body having an approximately tubular shape extending along a longitudinal axis, wherein the main body is formed of a first resin material;
an elastic member comprising a first end portion and a second end portion, wherein the elastic member is formed of a second resin material having a larger flexural modulus than the first resin material; and
a first treated layer arranged between an end portion of the main body and the first end portion of the elastic member, wherein the first treated layer is formed of a functional group that joins the end portion of the main body and the first end portion of the elastic member,
wherein the second end portion of the elastic member extends from the first end portion of the elastic member toward a central portion side of the main body along the longitudinal axis and radially away from the main body,
wherein a melting temperature of the second resin material is higher than a melting temperature of the first resin material, and the first end portion of the elastic member is joined to the end portion of the main body at a temperature equal to or higher than the melting temperature of the first resin material and lower than the melting temperature of the second resin material,
wherein the second resin material is fluororesin, and
wherein the first treated layer is formed by chemically treating an outer circumferential surface of the first end portion of the elastic member so that a surface reforming of the outer circumferential surface of the first end portion is performed.
2. The medical stent according to claim 1, wherein
the first resin material is polyurethane resin, and a hydroxy group or a carbonyl group in the first treated layer is bonded to a functional group of the polyurethane resin to join the end portion of the main body and the first end portion of the elastic member.

3. The medical stent according to claim 1, further comprising:
a coil formed by winding a wire around a given axis, wherein the coil is arranged on an inner circumference side of the main body coaxially along the longitudinal axis with the main body; and
an inner layer having an approximately tubular shape, wherein the inner layer is arranged on an inner circumference side of the coil coaxially along the longitudinal axis with the main body.

4. The medical stent according to claim 1, wherein the elastic member comprises a plurality of elastic members, the number of the plurality of elastic members being an odd number wherein the plurality of elastic members are provided with equal angles therebetween around the longitudinal axis.

5. The medical stent according to claim 1, further comprising:
a fixing member mounted on the outer circumferential surface of the first end portion of the elastic member and an outer circumferential surface of the main body, wherein the fixing member has an approximately tubular shape and is formed of the first resin material, wherein the outer circumferential surface of the main body is welded to an inner circumferential surface of the fixing member; and
a second treated layer arranged between the fixing member and the first end portion of the elastic member, and wherein the second treated layer and the inner circumferential surface of the fixing member are connected to each other at a temperature equal to or higher than the melting temperature of the first resin material and lower than the melting temperature of the second resin material.

* * * * *

UNITED STATES PATENT AND TRADEMARK OFFICE
CERTIFICATE OF CORRECTION

| | | |
|---|---|---|
| PATENT NO. | : 8,685,081 B2 | Page 1 of 1 |
| APPLICATION NO. | : 13/483564 | |
| DATED | : April 1, 2014 | |
| INVENTOR(S) | : Toshihiro Yamagata | |

It is certified that error appears in the above-identified patent and that said Letters Patent is hereby corrected as shown below:

Title Page, item (54) and in the Specification, Column 1, line 1,

It should read:

MEDICAL STENT AND PRODUCTION METHOD OF MEDICAL STENT

Signed and Sealed this
First Day of December, 2015

Michelle K. Lee
*Director of the United States Patent and Trademark Office*